United States Patent [19]
Brown

[11] Patent Number: 6,092,769
[45] Date of Patent: Jul. 25, 2000

[54] BREAST PROSTHESIS PROTECTIVE CRADLE

[76] Inventor: Clark D. Brown, 968 Tamarind Cir., Rockledge, Fla. 32955

[21] Appl. No.: 09/382,367

[22] Filed: Aug. 24, 1999

Related U.S. Application Data

[63] Continuation-in-part of application No. 09/017,887, Feb. 3, 1998, abandoned.

[51] Int. Cl.[7] ....................................................... F16H 11/38
[52] U.S. Cl. .......................... 248/166; 248/150; 248/431; 623/7
[58] Field of Search ....................................... 248/166, 165, 248/150, 431, 164, 174; 5/98.3, 648, 643, 127; 108/5, 25, 115, 3; 206/438, 570; 623/7, 8

[56] References Cited

U.S. PATENT DOCUMENTS

| | | |
|---|---|---|
| 250,878 | 12/1881 | Brush . |
| D. 274,390 | 6/1984 | Shakas ........................ 5/98.3 |
| D. 351,337 | 10/1994 | Weber-Unger ........................ D3/289 |
| 486,602 | 11/1892 | Morton ........................ 108/3 |
| 778,735 | 12/1904 | Becker ........................ 108/25 |
| 3,430,954 | 3/1969 | Massey ........................ 272/62 |
| 3,839,754 | 10/1974 | Hooper ........................ 5/98 A |
| 4,750,619 | 6/1988 | Cohen ........................ 206/438 |
| 4,852,743 | 8/1989 | Ridgeway ........................ 206/583 |
| 4,941,453 | 7/1990 | Shakas ........................ 5/98.3 |
| 4,974,525 | 12/1990 | Sheffield ........................ 108/118 |
| 5,037,436 | 8/1991 | Heaston ........................ 623/7 |
| 5,146,635 | 9/1992 | Gastle, et al. ........................ 5/620 |
| 5,316,147 | 5/1994 | Weber-Unger ........................ 206/438 |
| 5,354,337 | 10/1994 | Hoy ........................ 623/7 |
| 5,490,292 | 2/1996 | Auburn ........................ 5/8 |
| 5,496,094 | 3/1996 | Schwartzkopf et al. ........................ 297/45 |

OTHER PUBLICATIONS

J.C. Penny Catalog Presents Jodee ®Post–Mastectomy Fashions, Fall/Winter 1999, pp. 1–40.

*Primary Examiner*—Leslie A. Braun
*Assistant Examiner*—Gwendolyn Baxter
*Attorney, Agent, or Firm*—Brian S. Steinberger; Law Offices of Brian S. Steinberger

[57] ABSTRACT

A portable and collapsible cradle for supporting any shaped breast prosthesis such as but not limited to a triangular shape, a teardrop shape and an asymmetrical shape in a natural nondeformed state. The platform has upside down U-shaped rods pivotally connected to one another by pins. Chains and cords having one expanded position and one collapsible position allow the rods to form a cross orientation to one another. A flexible material having a central stretchable portion surrounded by a fabric material is supported in a trampoline fashion by the rods. Fasteners such as hook and loop, and snaps allow flap edges on the material to wrap about portions of the U-shaped rods and the chains/cords. The stretchable portion of the material allows for all types of breast prosthesis to be supported in a natural undeformed state. The material can include filly doily edges for giving the cradle a pleasingly aesthetic appearance when assembled. All surfaces of all of the components of the cradle having nonrough edges so as not to be able to puncture the breast prostheses. The one collapsed position of the cradle allows the cradle to be held within a narrow sleeve shaped carrying bag, so that the cradle can subsequently be removed from the bag and be pivotally opened into the expanded position without additional assembly of any components.

19 Claims, 5 Drawing Sheets

BREAST PROSTHESIS PROTECTIVE CRADLE

This invention relates to breast prostheses, and in particular to a portable and collapsible cradle support for allowing any shaped breast prostheses to be aesthetically and safely supported in a natural undeformed state, and is a Continuation-In-Part of U.S. application Ser. No. 09/017,887 filed on Feb. 3, 1998 now abandoned.

BACKGROUND AND PRIOR ART

Breast prostheses have become more common place with women who have had a mastectomy. The typical prosthesis is formed of a gelatinous and pliable material within a flexible skin material that resembles a woman's breast. There are several types of breast prostheses currently available. For example, typical types of breast prosthesis forms having triangular shapes, teardrop shapes and asymmetrical shapes. The type of shape that is used is usually determined by the type of surgery that was performed. Page 22 of the J.C. Penney Fall/Winter 1999 Catalog Presents Jodee Postmastectomy Fashions describes these well known types of breast prosthesis forms.

All of the breast prostheses has a tendency to deform out of shape when not being worn. Current methods of storing the prosthesis have also added to the deformations to the prosthesis over time. For example, the typical prosthesis is sold in a cardboard type box that is not reusable. The typical packing materials such as plastic and crushed paper in the packing boxes do not adequately support the prosthesis during times of nonuse. These packing boxes cannot be constantly reused over time, and are very large and take up allot of room.

Additionally, the breast prosthesis has a tendency to absorb the imprint of the surface that the prosthesis is supported by. For example, when used with a brassiere the breast prosthesis forms wrinkles on the surface thereof as a mirror image of the generally stiff brassiere material.

When not being used wearers have been forced to resort to slinging the prosthesis over a door knob or the top of the door itself when the prosthesis is not being used. Leaving the prosthesis in open areas such as on door knobs, tops of doors, on the tops of dresser drawers and sink tops is also not aesthetically pleasing nor pleasant to the wearer. The problems of storage become even a greater concern when the wearer is traveling and now needs a clean surface for temporary storage which is difficult to find in places such as hotel rooms and such.

Attempts have been made over the years to overcome these storage problems. U.S. Pat. No. 5,037,436 Heaston describes a support for a breast prosthesis having an inflatable bladder. The Heaston '436 patent requires the user to blow into a valve to fill a balloon type support. Besides the unsanitary requirement of making the user blow into the valve, the plastic type bladder material would be useless with even a single pinhole leak and would be useless over time. Women with new breast cancer or lung cancer cannot "blow" easily.

U.S. Pat. No. 5,316,147 and Des.351,729 to Wever-unger and U.S. Pat. No. 4,750,619 to Cohen et al. each describe cases for receiving breast prosthesis. However, the cases appear as bulky packing boxes which are not collapsible during transport. Besides not being aesthetic, all of these devices would tend to cause attention to be focused at the storage device itself, which is not what the wearer would desire.

U.S. Pat. No. 5,354,337 to Hoy describes a breast prosthesis support having a cup support with vertical legs. However, the Hoy '337 legs are inserted by dowel ends into receptacles and must be completely removed when disassembled which results in several loose pieces when being transported. Having plural leg parts increases the chance of losing a leg during transport. Additionally, the "bra..cup" shape of Hoy only allows for the tear drop breast prosthesis shape to be supported. Hoy's limited shape would not be able to adequately support the triangular and asymmetrical shape breast prostheses.

U.S. Pat. No. 5,146,635 to Gastle et al. describes a veterinary surgery table that must be large enough to support a "calf" during surgery procedures. Besides being unduly large and cumbersome and not able to be easily transported, Gastle requires adjustable "buckles" that have inherently sharp and protruding surface edges which would easily puncture and otherwise damage a breast prosthesis. Furthermore, the buckles would have to be constantly adjusted when being used and taken apart. Finally, Gastle has no planar support surface for supporting the entire prosthesis. Instead the straps and buckles would easily cause surface indentations on a pliable breast prostheses.

U.S. Pat. No. 4,974,525 to Sheffield describes a "folding table apparatus" which also has sharp surface edges such as visible hooks for holding its' chains. During assembly and disassembly, the chains would have to be unhooked and rehooked and desirable hook positions would have to be constantly reinvented. Additionally, Sheffield describes using a flat hard type planar surface which would flatten out a breast prosthesis and not allow a breast prosthesis to be supported in a natural undeformed state.

U.S. Pat. No. 3,839,754 to Hooper describes a "folding baby cot" that has many sharp protruding surface edges such as exposed metal edged holes, protruding metal buttons, sharp rivets and the like, which can easily damage a breast prosthesis. Besides being unduly large and cumbersome to transport, Hooper requires substantial disassembly for transport, such as removing rigid telescoping tubes. Additionally, the "canvas" type support material in Hooper would not allow a breast prosthesis to be supported in a nondeformed state, and instead would flatten the shape of the breast prosthesis.

SUMMARY OF THE INVENTION

The first objective of the present invention is to provide a portable collapsible support for a breast prosthesis.

The second object of the present invention is to provide a cradle support for a breast prosthesis that allows all types of breast prostheses such as but not limited to a triangular, teardrop and asymmetrical shapes to be supported and stored in a natural nondeformed state when not being worn.

The third object of this invention is to provide a support and storage apparatus for a breast prosthesis that is aesthetically pleasing to the eye and decor of the home.

The fourth object of this invention is to provide a narrow sleeve bag for allowing a breast prosthesis support and storage apparatus to be safely and easily carried and transported.

A preferred embodiment of the novel breast prosthesis cradle includes a first and second upside down U-shaped aluminum support rod which is pivotally connected to one another by pins. Flexible longitudinal means having only a single expanded position and a single collapsed position, such as chains and cords hold the rods in a cross orientation to one another.

A substantially rectangular flexible platform formed having a central nylon type stretchable material surrounded by a fabric material that can be suspended by the rods and the longitudinal means by overlapping flap edges. The flap edges can have fasteners thereon such as hook and loop fasteners and snaps for allowing the flap edges to wrap about the rods and longitudinal means and be connected to another portion of the flap edges. The substantially rectangular central nylon type stretchable material has a general natural indentation for supporting all types of breast prostheses such as but not limited to triangular, teardrop and asymmetrical shapes in a non deformed relaxed state. The flexible platform can include frilly doily type edges for overlying upper edges of the tops of the rods to give the cradle anesthetic appearance. A detachable pad with hook and loop fasteners on and under surface can also be connected to the flexible material platform.

All surface areas on all of the components in the invention have nonrough edges such as being rounded, curved and smooth so as not to puncture and damage the fragile supported breast prosthesis.

A novel narrow sleeve fabric material carrying bag allows the collapsed position of the cradle apparatus to be easily inserted therein for transport and storage. No extra assembly is necessary for the cradle apparatus when changing the cradle apparatus from an expanded positioned to a collapsed position and vice versa.

Further objects and advantages of this invention will be apparent from the following detailed description of a presently preferred embodiment which is illustrated schematically in the accompany drawings.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Figure 1:
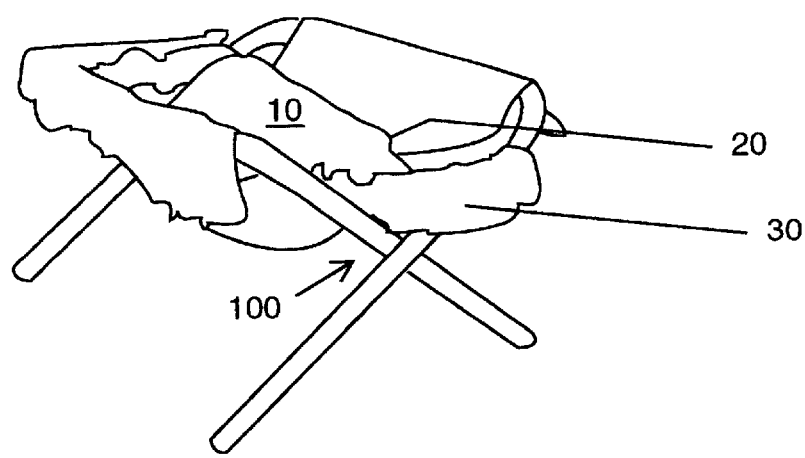
FIG. 1 is a perspective view of a breast prosthesis portable cradle.
Figure 2:
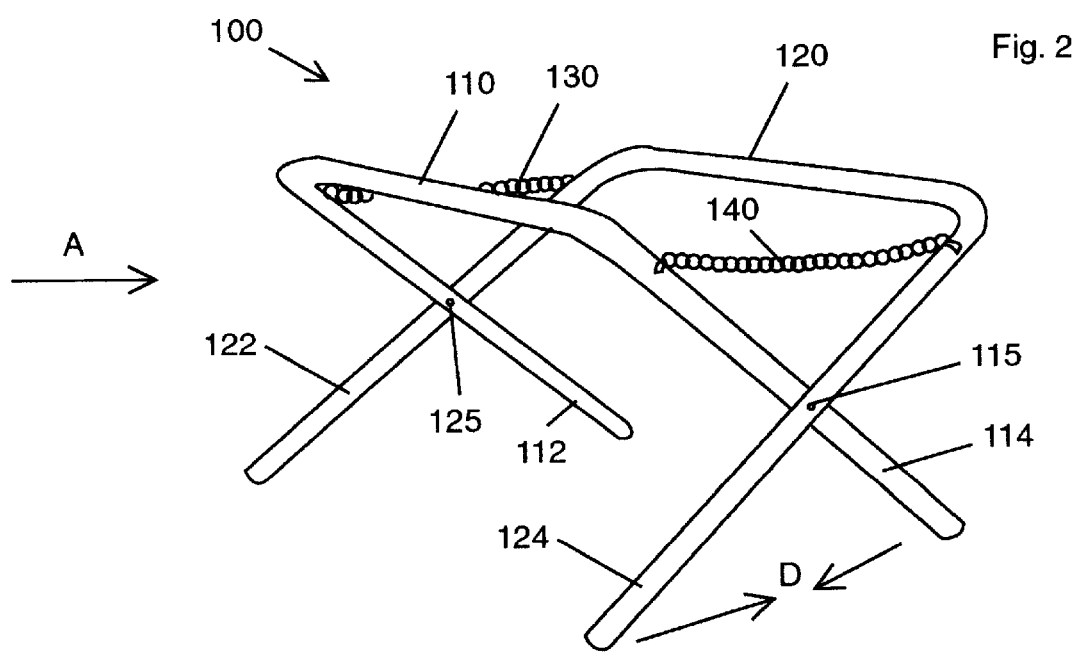
FIG. 2 is a perspective view of the cradle support stand for the cradle.
Figure 3A:
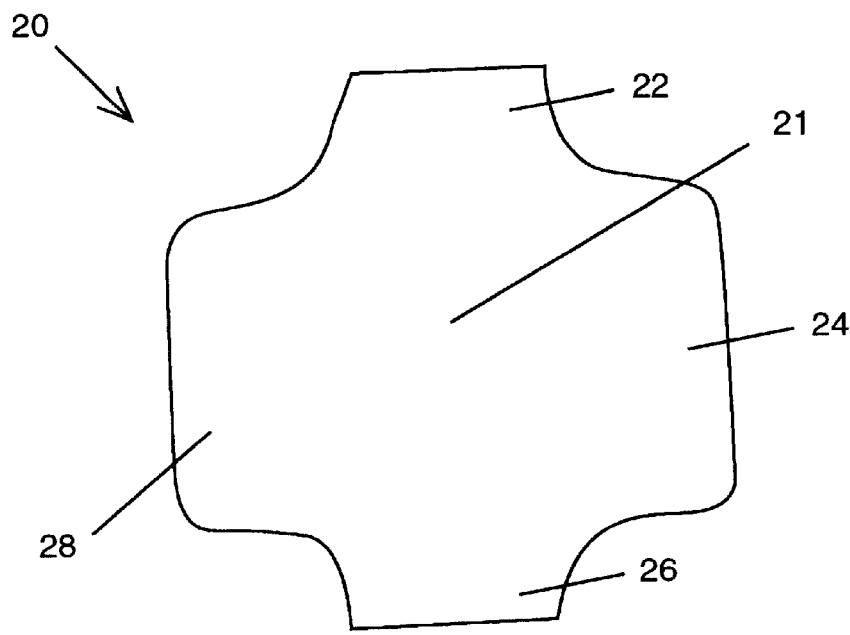
FIG. 3A is a top view of the pad insert for the cradle of FIG. 1.
Figure 3B:
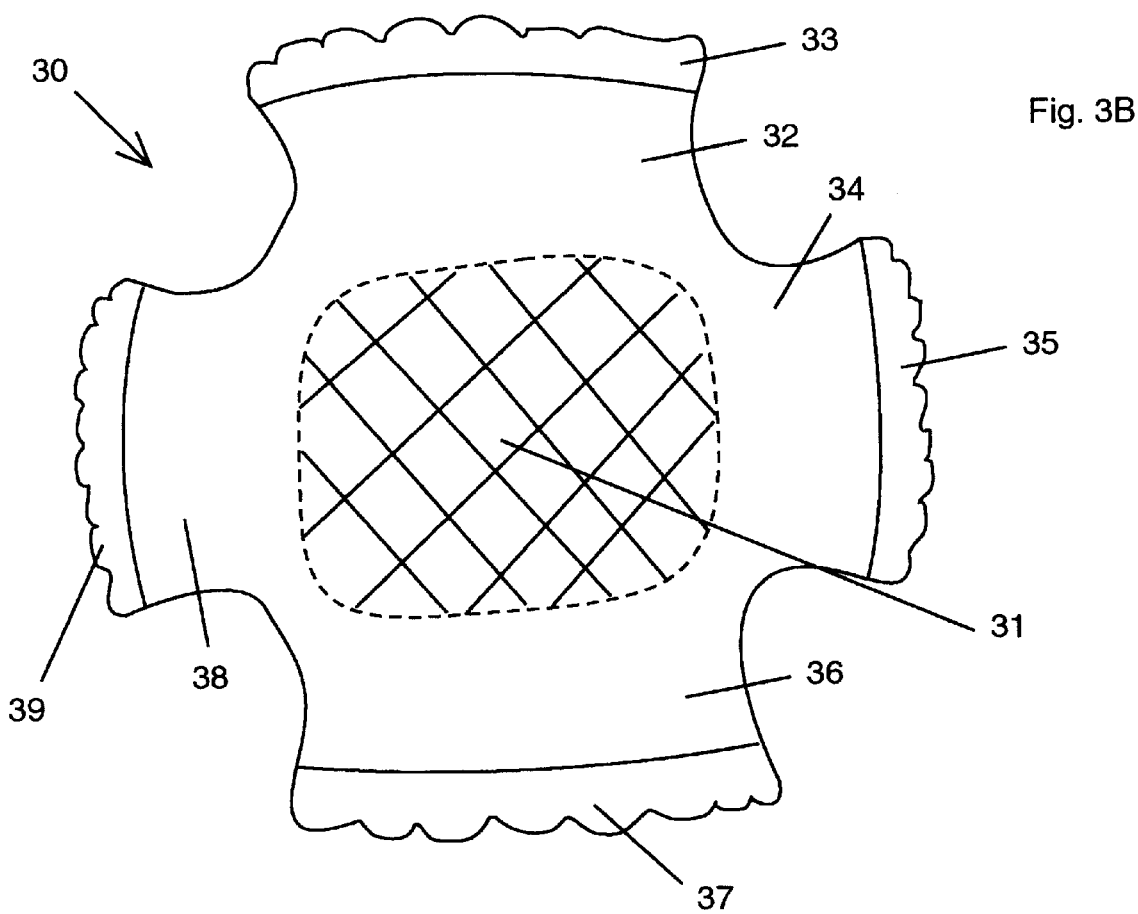
FIG. 3B is a top view of the cover for use with the cradle of FIG. 1.

FIG. 1 is a perspective view of a breast prosthesis portable cradle 1, which includes a breast type prosthesis 10 which is substantially supported by a pad insert 20 inside a base cover 30. FIG. 2 is a perspective view of the cradle support stand 100 for the cradle 1 of FIG. 1. FIG. 3A is atop view of the pad insert 20 for the cradle 1 of FIG. 1. Pad insert 20 can be made from a felt material 21 with four rectangular flap edges 22,24,26,28, respectively. FIG. 3B is a top view of the base cover 30 for use with the cradle 1 of FIG. 1. Base cover 30 can include a stretchable material center 31 portion such as stretchable nylon netting material. The stretchable center portion can directly support the breast prosthesis thereon. Optionally, the pad 20 can be laid upon the surface of the stretchable center portion 31.

Surrounding the central stretchable portion and sewn thereto is a second material having rectangular flap edges 32, 34, 36, and 38, formed of a fabric material such as but not limited to cotton, and the like. Each of the flap edges 32, 34, 36, 39 can include outer edges 33, 35, 37, 39 formed of a frilly edged fabric, similar to that of a doily, that gives the cradle 1, a pleasingly aesthetic appearance. The center portion 31 of the cover by itself and in combination with the pad 20 as shown in FIG. 1, form a downward curved indentation to allow the breast prosthesis 10 to be substantially supported therein while maintaining its' natural curved shape. Cover 30 can easily support all types of breast prosthesis forms such as but not limited to triangular, teardrop and asymmetrical shapes thereon in a natural non deformed state.

Figure 3C:
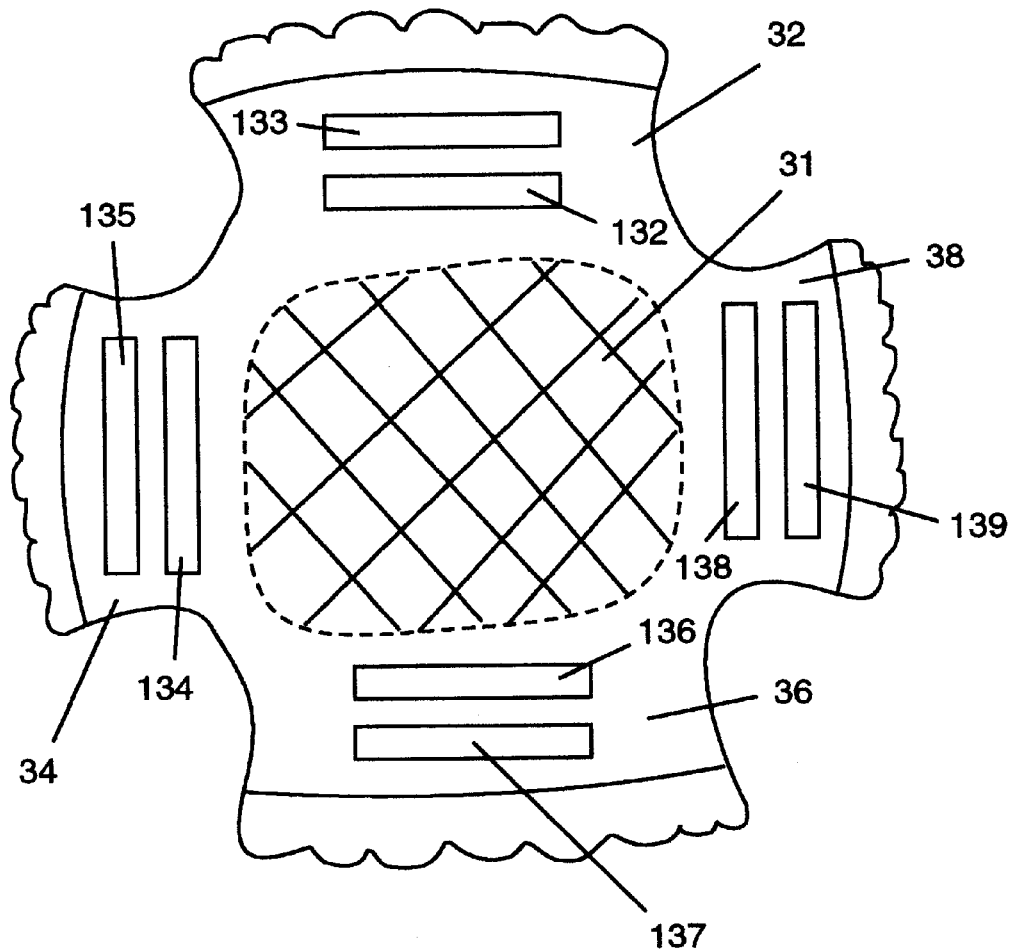
FIG. 3C is a bottom view of the cover for use with the cradle of FIG. 1.
Figure 3D:
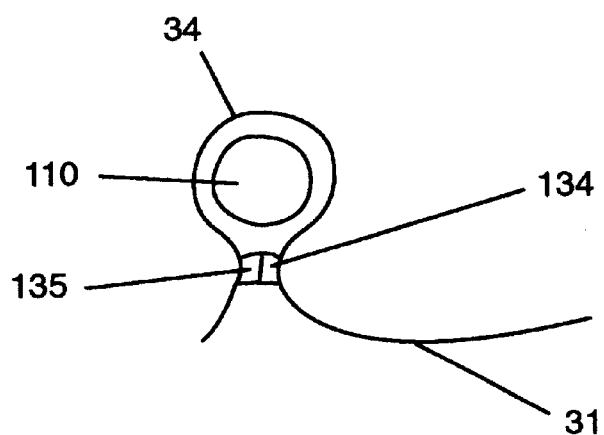
FIG. 3D is an enlarged cross-sectional view of a flap edge wrapped about a horizontal member.

FIG. 3C is a bottom view of the cover for use with the cradle of FIG. 1. Connected to the undersurface are fastener pairs 132–133, 134–135, 136–137, 138–139 on each of the flap edges 32, 34, 36, 38. The fasteners can be such as but not limited hook and loop fasteners, mateable snaps, and the like. The fastener pairs allow for each of the flap edges to wrap about each of the horizontal members 110, 120, 130, 140 of the cradle invention when the cradle is in its' single expanded position as shown in FIG. 2. When wrapped about their respective horizontal member, each of the fastener pairs can attach to one another as shown in FIG. 1. FIG. 3D is an enlarged cross-sectional view showing a flap edge 34 wrapped about a horizontal member 110 with fasteners 134–135 connected to one another.

Figure 4:
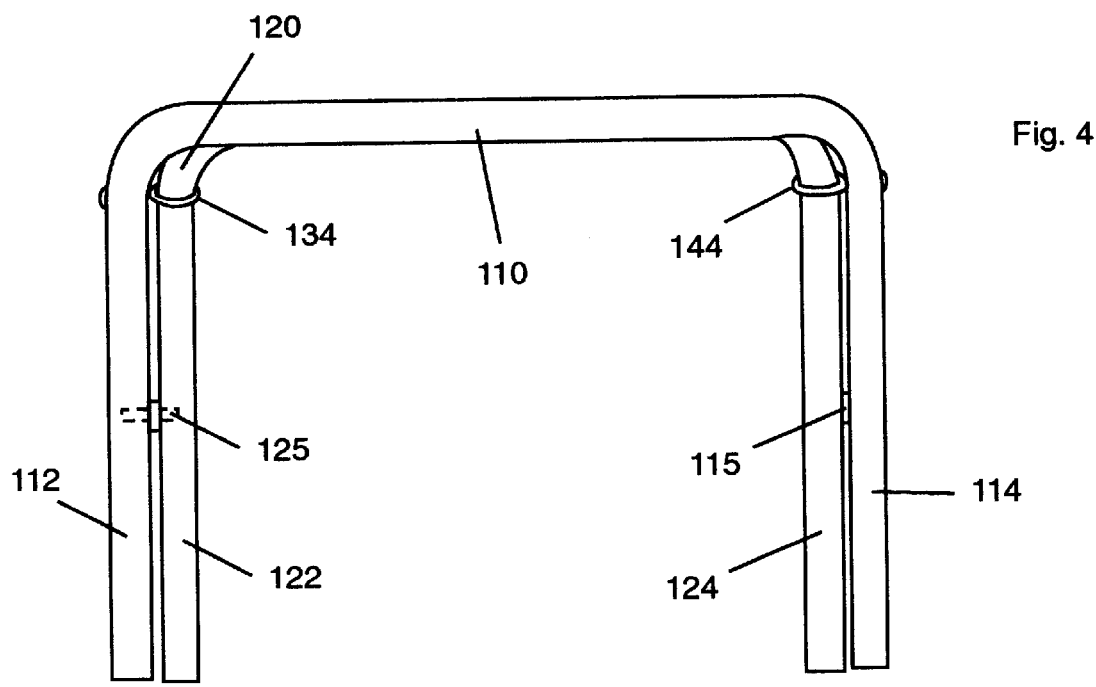
FIG. 4 is a side view of the stand of FIG. 2 along arrow A.
Figure 5:
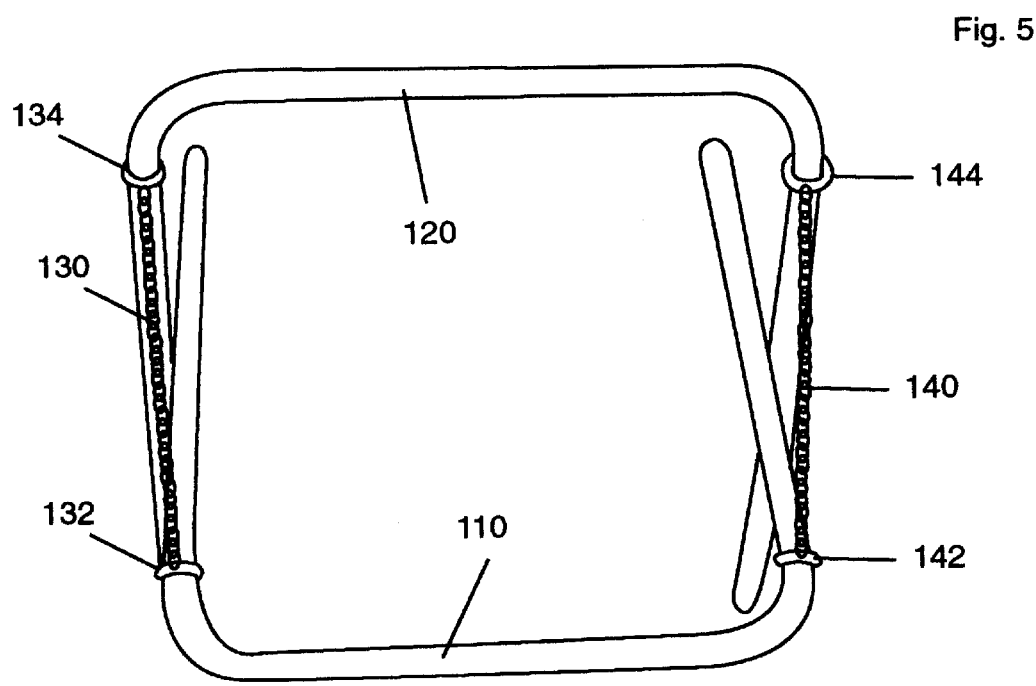
FIG. 5 is a top view of the stand of FIG. 2 along arrow B.

FIG. 4 is a side view of the stand 100 of FIG. 2 along arrow A. FIG. 5 is a top view of the stand 100 of FIG. 2 along arrow B. Referring to FIGS. 2, 4 and 5, stand 100 includes two upside down U-shaped aluminum rods 110, 120 with horizontal bars and respective vertical legs 112, 114 and 122, 124. Brass pins 115, 125 about midway down the respective vertical legs 112, 122 and 114, 124 allow the U-shaped rods 110, 120 to pivotally connect to one another. Nonrigid longitudinal means 130, 140 having one expanded position and one collapsed position allow the U-shaped rods 110, 120 to move between the one expanded and one collapsed positions. In one embodiment, smooth edge D-rings 132, 134, 142, 144, can connect nonrough edged chains 130 and 140 to respective bent rods 110, 120, and allow the cradle stand 100 to be in a cross orientation assembled state. Alternatively, other types of nonrigid longitudinal means such as nylon cords, and the like, also having one expanded position and one collapsed position can be used.

Flap edges 32, 34, 36, 38 of base cover 30 can overly both the chains 130, 140 and horizontal members of the bent rods 110, 120 with the fastener pairs 132–133, 134–135, 136–137, 138–139 connected to one another. Moving the vertical legs inward in the direction of arrow D as shown in FIG. 2, collapses the stand to be flattened and which allows it to be stored in the most smallest of places such as a drawer and/or suitcases for travel. Thus, the base cover 30 can be left on the cradle during the collapsed state without having to be removed from the rest of the cradle. The removable fastener pairs allow the base cover 30 to be removed when it necessary for cleaning and the like.

All surface areas of the invention have non rough edges so as to eliminate the chances that any component can damage and puncture the breast prosthesis supported thereon.

Figure 6:
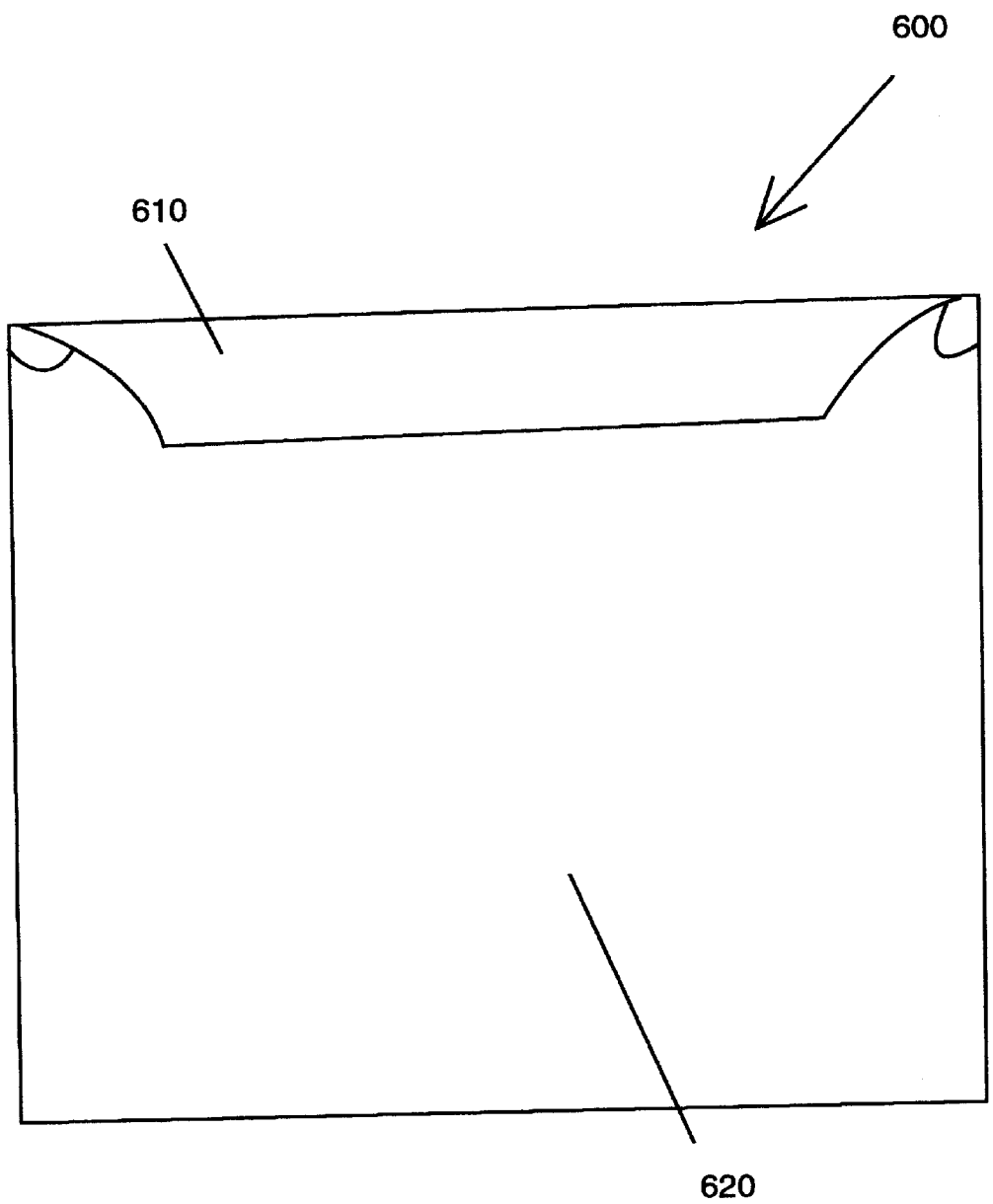
FIG. 6 is a perspective view of the novel narrow sleeve carrying bag for holding a collapsed version of the cradle of the preceding figures.

FIG. 6 shows the novel narrow sleeve carrying bag 600 that can be made of fabric and the like for holding a collapsed version of the novel cradle apparatus inside. A flap cover 610 can open the top of the bag 600 to a narrow inner compartment 620 that can hold a collapsed version of the cradle invention therein.

While the invention has been described, disclosed, illustrated and shown in various terms of certain embodiments or modifications which it has presumed in practice, the scope of the invention is not intended to be, nor should it be deemed to be, limited thereby and such other reserved especially as they fall within the breadth and scope of the claims here appended.

I claim:

1. A collapsible cradle apparatus supporting a breast prosthesis, comprising in combination:

a first upside down U-shaped support having a first substantially horizontal upper member with a first set of rod legs;

a second upside down U-shaped support having a second substantially horizontal upper member with a second set of rod legs, pivotally connected to the first upside down U-shaped support;

two flexible nonrigid, rounded and smoothed surface longitudinal means, each having one expanded position and one collapsed position, for connecting and holding both the first support and the second support in a substantially cross orientation to one another, each of the connecting means being connected to each of the first set of rod legs and the second set of rod legs adjacent to each of the horizontal upper members; and a substantially rectangular flexible sheet having four flap edges, the flexible sheet being solely supported and suspended by overlying the flap edges on both the first and the second horizontal upper members and on both the connecting means, wherein the flexible sheet forms a substantially rectangular platform that supports and cradles said breast prosthesis in a non deformed state and so as not to puncture the breast prosthesis.

2. The collapsible cradle apparatus of claim 1, wherein the two connecting means includes:

chains having smooth edges.

3. The collapsible cradle apparatus of claim 1, wherein the two connecting means includes:

cords having smooth edges.

4. The collapsible cradle apparatus of claim 1, further comprising:

fasteners for wrapping each of the four flap edges about each of the first support, the second support and the two connecting means.

5. The collapsible cradle apparatus of claim 4, wherein the fasteners are only located on the four flap edges.

6. The collapsible cradle apparatus of claim 4, wherein the fasteners are chosen from at least one of:

hook and loop fasteners and snap fasteners.

7. The collapsible cradle apparatus of claim 1, wherein the substantially rectangular flexible sheet includes:

a stretchable netting material for supporting the breast prosthesis; and a fabric material surrounding the netting material.

8. The collapsible cradle apparatus of claim 1, wherein the stretchable netting material includes:

a nylon material.

9. The collapsible cradle apparatus of claim 1, further comprising:

a carrying bag sleeve for holding the one collapsed position of the cradle apparatus therein.

10. The collapsible cradle apparatus of claim 1, wherein the stretchable netting material includes:

a nylon material.

11. The collapsible cradle apparatus of claim 1, further comprising:

a carrying bag sleeve for holding the one collapsed position of the cradle apparatus therein.

12. The collapsible cradle apparatus of claim 1, wherein the breast prosthesis can include any one of a triangular shape, a teardrop shape, an asymmetrical shape.

13. A collapsible cradle apparatus supporting a breast prosthesis, comprising in combination:

a first bent support rod having a first upper substantially horizontal member with a first set of rod legs;

a second bent support rod having a second upper substantially horizontal member with a second set of rod legs;

means for pivotally connecting the first bent support rod to the second bent support rod;

two connecting nonrigid, and non puncturable surface extendible means, each having one expanded position and one collapsed position, for holding the first bent support rod and the second bent support rod in cross orientation to one another; and a substantially rectangular connecting platform sheet having four flap edges, the flexible platform sheet being solely suspended by the flap edges overhanging both the first upper substantially horizontal member and the second upper substantially horizontal member and the two extendible holding means, wherein the rectangular flexible sheet supports and cradles said breast prosthesis in a non deformed state having no rough surface edges so as not to puncture the breast prosthesis.

14. The collapsible cradle apparatus of claim 13, wherein the two extendible holding means includes:

chains having smooth edges.

15. The collapsible cradle apparatus of claim 13, wherein the two flexible nonrigid, rounded and smoothed surface longitudinal means includes:

cords having smooth edges.

16. The collapsible cradle apparatus of claim 13, further comprising:

fasteners for wrapping each of the four flap edges about each of the first and second horizontal members and the two extendible holding means.

17. The collapsible cradle apparatus of claim 16, wherein the fasteners are only located on the four flap edges.

18. The collapsible cradle apparatus of claim 16, wherein the fasteners are chosen from at least one of:

hook and loop fasteners and snap fasteners.

19. The collapsible cradle apparatus of claim 13, wherein the substantially rectangular flexible sheet includes:

a stretchable netting material for supporting the breast prosthesis; and a fabric material surrounding the netting material.

* * * * *